US012763170B2

(12) United States Patent
Arabi et al.

(10) Patent No.: US 12,763,170 B2
(45) Date of Patent: Oct. 13, 2026

(54) METHOD, SYSTEM, AND TOOL FOR CREATING, FILTERING, AND SELECTING MOLECULES IN DRUG DESIGN FOR THERAPEUTIC EFFECTS

(71) Applicant: UNITED ARAB EMIRATES UNIVERSTIY, Al Ain (AE)

(72) Inventors: Alya A. Arabi, Al Ain (AE); Alaa M. A. Osman, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 17/990,703

(22) Filed: Nov. 20, 2022

(65) Prior Publication Data

US 2024/0177808 A1 May 30, 2024

(51) Int. Cl.
*G16C 10/00* (2019.01)
*G16C 20/50* (2019.01)

(52) U.S. Cl.
CPC ............ *G16C 10/00* (2019.02); *G16C 20/50* (2019.02)

(58) Field of Classification Search
None
See application file for complete search history.

(56) References Cited

U.S. PATENT DOCUMENTS 11,161,827 B2 11/2021 Zhang et al.

OTHER PUBLICATIONS

Arabi. Atomic and molecular properties of nonclassical bioisosteric replacements of the carboxylic acid group. Future Med Chem 2020, 12(12), pp. 1111-1120 (Year: 2020).*
Kumari et al. Amide bond bioisosteres: Strategies, Synthesis, and Successes. J. Med. Chem. 2020, vol. 63, pp. 12290-12358 (Year: 2020).*
Milani et al. Bioisosteric Modification of To042: Synthesis and Evaluation of Promising Use-Dependent Inhibitors of Voltage-Gated Sodium Channels. ChemMedChem. Dec. 6, 2021; 16(23):3588-3599. (Year: 2021).*
Wilcken R, Zimmermann MO, Bauer MR, Rutherford TJ, Fersht AR, Joerger AC, Boeckler FM. Experimental and Theoretical Evaluation of the Ethynyl Moiety as a Halogen Bioisostere. ACS Chem Biol. Dec. 18, 2015;10(12):2725-32. (Year: 2015).*
Osman, Alaa MA, and Alya A. Arabi. "Average Electron Density: A Quantitative Tool for Evaluating Non-Classical Bioisosteres of Amides." ACS Omega Mar. 5, 2024 (Year: 2024).*
Lage, O.M.; Ramos, M.C.; Calisto, R.; Almeida, E.; Vasconcelos, V.; Vicente, F. Current Screening Methodologies in Drug Discovery for Selected Human Diseases. Mar. Drugs 2018, 16, 279 (Year: 2018).*
Matta et al., "The bioisosteric similarity of the tetrazole and carboxylate anions: clues from the topologies of the electrostatic potential and of the electron density," European Journal of Medicinal Chemistry, vol. 45, Issue 5, May 2010.
Matta et al., "Electron Density Descriptors as Predictors in Quantitative Structure-Activity/Property-Relationships and Drug Design," Future Medicinal Chemistry, vol. 3, No. 8, Jun. 27, 2011.
Arabi et al., "Electrostatic Potentials and Average Electron Densities of Bioisosteres in Methylsquarate and Acetic Acid," Future Medicinal Chemistry, vol. 8, No. 4, Mar. 15, 2016.
Arabi, "Route to Drug Design via Bioisosterism of Carboxyl and Sulfonamide Groups," Future Medicinal Chemistry, vol. 9, No. 18, Nov. 9, 2017.
Arabi, "Quantitative Evaluation of Bioisosteres in Drug Design," Compbiomed-Conference, 2019.
Arabi, "Artificial Intelligence in Drug Design: Algorithms, Applications, Challenges and Ethics," Future Drug Discovery, vol. 3, No. 2, Apr. 29, 2021.
Arabi, "Atomic and molecular properties of nonclassical bioisosteric replacements of the carboxylic acid group," Future Medicinal Chemistry, vol. 12, No. 12., May 13, 2020.

* cited by examiner

*Primary Examiner* — Kaitlyn L Minchella
*Assistant Examiner* — Jonathan Edward Hayes
(74) *Attorney, Agent, or Firm* — Nath, Goldberg & Meyer; Joshua B. Goldberg

(57) ABSTRACT

A system and method for identifying bioisosteres of a molecule are provided. These methods are particularly useful for confirming that amides and 1,2,3-triazoles are bioisosteres of one another. The methods for evaluating bioisosteres of a molecule include selecting a first molecule of interest having an amide group as a first bioisostere, replacing the amide group with a 1,2,3-triazole group as a second bioisostere to obtain a second molecule, completing a quantum mechanics (QM) simulation for each molecule, calculating average electron density (AED) values corresponding to the first and second bioisosteres in the first and second molecules, respectively, and confirming the bioisosterism based on the calculated AED values of the biosiosteres. These methods can be further used to identify further bioisosteres thereof. The present methods and systems can be used to aid in many applications including but not limited to the development of drug design.

11 Claims, 1 Drawing Sheet

METHOD, SYSTEM, AND TOOL FOR CREATING, FILTERING, AND SELECTING MOLECULES IN DRUG DESIGN FOR THERAPEUTIC EFFECTS

BACKGROUND

1. Field

The disclosure of the present patent application relates to methods and systems for identifying bioisosteres of a molecule, particularly to confirm that 1,2,3-triazoles and amides are bioisosteres of one another, and to identify further bioisosteres thereof. The present methods and systems can be used to aid in many applications including but not limited to the development of drug design.

2. Description of the Related Art

In general, various chemical and other physical properties of various molecules can be classified by numerous tools. For example, methods of using electron density to quantify the mean positions of atoms in chemical compounds, their chemical bonds, and other information are currently generally known. This is particularly important for drug molecules, where minor changes in a drug molecule's structure can significantly affect its biological activity. One particularly useful tool to meet these challenges is the investigation, identification, classification, and analysis of various bioisosteres of a molecule.

One of the noticeable substitutions in drug design is bioisosteric replacement, where the chemical properties of a molecule significantly change while the biological activity remains intact. Bioisosteres are substituents or groups that impart similar biological properties to a chemical compound; for example, the bioisosteric replacement of a hydrogen atom with a fluorine atom within a drug molecule will generally have no influence on the drug's efficacy, but it may prolong the drug's half-life by inhibiting metabolic oxidation. Thus, the purpose of exchanging one bioisostere for another is to fine tune the pharmacokinetic or pharmacodynamic properties of a bioactive compound.

Examples of bioisosteres in the literature include classical and non-classical ones. The classical bioisosteres are isoelectronic at the valence shell. This isoelectronic factor is typically the accepted attribution to the similarities in the biological activity of drug molecules that involve substituted classical bioisosteres. The chemical and physical basis of equivalence for most classical bioisoteric substitutions is obvious (e.g., hydrogen to fluorine, ester to amide, phenyl to thiophene).

The case with non-classical bioisosteric replacements is not as trivial as the common factor among them is not obvious. For such non-classical bioisosteric substitutions, the physicochemical similarities between the two bioisosteres are not readily apparent. The bioisosteric equivalence of carboxylate and tetrazole is an example of the latter. In this example, tetrazole and carboxylate anion have been interchanged in the development of non-steroidal anti-inflammatory drugs. Although these two functional groups appear to be structurally quite different, numerous studies have demonstrated the clear bioisosteric relationship between carboxylate and tetrazole in neurotransmitters such as gamma-aminobutyric acid and in drugs such as gabapentin. In such instances, tetrazole is believed to be a desirable bioisosteric replacement for carboxylate because it is more lipophilic, thus traversing the blood-brain barrier more easily than the anionic carboxylate group, while not detracting from the compound's final receptor-mediated activity.

Typically, similarities in electrostatic potential (ESP) maps are considered as the common factor for non-classical bioisosteres. However, relying exclusively on ESP maps for explaining the similarity in the biological activity of non-classical bioisosteres has some gaps. One of the gaps evolves around the qualitative aspect of this tool, which introduces possibilities of bias in deciding whether similarities are depicted or not. Another gap is the occasional failure to exhibit similarities for known bioisosteres. It is thus crucial to have a quantitative tool to evaluate bioisosteres. While such tools have been reported as under development for classical bioisosteres, there are currently no working tools available to reliably, quantitatively, determine bioisosterism between non-classical bioisosteres.

Thus, there remains a need for an a priori method with which to demonstrate the physical similarities between non-classical bioisosteres, regardless of any isomerism or capping changes therebetween.

SUMMARY

The methods and systems described herein relate to the identification and classification of various bioisosteres of a molecule, particularly non-classical bioisosteres. More specifically, the present methods and systems relate to a new use of the quantum theory of atoms in molecules (QTAIM) and the Average Electron Density (AED) quantitative tools, used in combination, to assist in developing, classifying, and confirming non-classical bioisosteres of one another. The present methods and systems can then be used to aid in the discovery of new bioisosteres of a molecule, thus aiding in drug design and development.

In one embodiment, the present subject matter relates to a method for evaluating similarities between bioisosteres of a molecule, the method comprising: selecting a first molecule of interest having an amide group as a first bioisostere; replacing the amide group of the first molecule of interest with a 1,2,3-triazole group as a second bioisostere to obtain a second molecule having the second bioisostere; completing a quantum mechanics (QM) simulation for the first and second molecules containing first and second bioisosteres; calculating average electron density (AED) values corresponding to the first and second bioisosteres in the first and second molecules; and confirming the experimentally observed bioisosterism between the 1,2,3-triazole group and the amide group based on the calculated AED values.

In another embodiment, the present subject matter relates to a for confirming 1,2,3-triazole-to-amide bioisosterism, the method comprising: selecting a first molecule of interest having an amide group as a first bioisostere; replacing the amide group of the first molecule of interest with a 1,2,3-triazole group as a second bioisostere to obtain a second molecule with the second bioisostere; completing a quantum mechanics (QM) simulation for the first and second molecules; calculating average electron density (AED) values corresponding to the first and second bioisosteres in the first and second molecules; and confirming the experimentally observed bioisosterism between the 1,2,3-triazole group and the amide group based on the calculated AED values.

In certain embodiments, each bioisostere can be classified regardless of an isomeric form of the first bioisostere or the second bioisostere. By way of non-limiting example, when the second molecule has the 1,2,3-triazole group, each bioisostere can be classified for 1,4-substituted or 1,5-substituted 1,2,3-triazole groups as two different isomeric forms of the 1,2,3-triazole group. Similarly, for example, when the first molecule has the amide group, each bioisostere can be classified for cis or trans amide groups as two different isomeric forms of the amide group.

In certain embodiments, the calculated average electron densities (AED) values can be calculated as a sum of electron population divided by a sum of volumes, of all atoms of the first or second bioisostere. Further, the calculated AED values of the first bioisostere and the second bioisostere may be equivalent to one another, irrespective of any groups to which the first bioisostere and the second bioisostere are attached. Stated differently, the calculated AED values of the first bioisostere and the second bioisostere may be equivalent to one another when the first bioisostere and the second bioisostere are capped with any groups, hypothetical or from real drug molecules. Similarly, the calculated AED values of the first bioisostere and the second bioisostere may be equivalent to one another regardless of whether they are docked to a receptor. Likewise, in certain embodiments, a portion of the first molecule not containing the first bioisostere and a portion of the second molecule not containing the second bioisostere have a common structure, perhaps even an identical structure, particularly for existing drug molecules.

In a further embodiment, the present subject matter relates to a method for discovering new bioisosteres of a molecule, the method comprising: selecting a first molecule of interest having an amide group as a first bioisostere; replacing the amide group of the first molecule of interest with a 1,2,3-triazole group as a second bioisostere to obtain a second molecule with the second bioisostere; evaluating similarities between the first bioisostere and the second bioisostere, particularly similarities in their respective AED valus; identifying the calculated AED values equivalent between the first and second bioisosteres; identifying additional sets of atoms having calculated AED values corresponding to the calculated AED values equivalent between the first and second bioisosteres; and replacing the amide group of the first molecule of interest with one of the identified additional sets of atoms to obtain a third molecule with a third bioisostere.

In this regard, in certain embodiments, the third bioisostere of the third molecule can be further evaluated to determine any commonalities in biological properties to the first bioisostere of the first molecule of interest. In certain embodiments, the third bioisostere of the third molecule will be found to share common biological properties with the first bioisostere of the first molecule of interest. Should this occur, the third bioisostere of the third molecule may be further investigated as a pharmaceutical of interest.

These and other features of the present subject matter will become readily apparent upon further review of the following specification.

DETAILED DESCRIPTION OF THE PREFERRED EMBODIMENTS

Definitions

Figure 1:
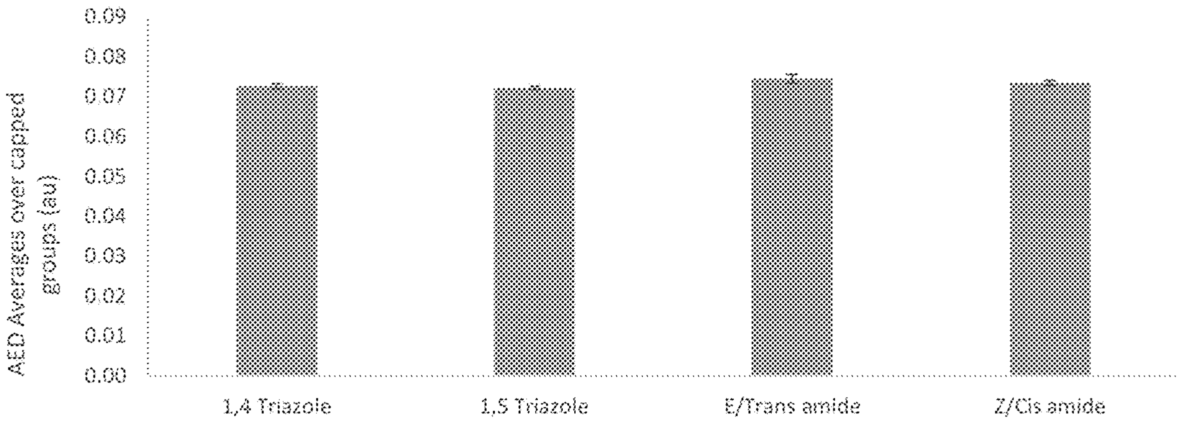
FIG. 1 shows average AEDs over all 9 capping groups of 1,2,3-triazole (1,4-triazole and 1,5-triazole) and amide (cis and trans) at an isodensity of 0.001 au.

As used herein, the terms "bioisostere", "bioisosteres", "bioisosterism", "bioisosteric", and the like are used interchangeably herein to refer to substituents or groups that impart similar biological properties to a chemical compound; for example, the bioisosteric replacement of a hydrogen atom with a fluorine atom within a drug molecule will generally have no influence on the drug's efficacy, but it may prolong the drug's half-life by inhibiting metabolic oxidation. Thus, the purpose of exchanging one bioisostere for another is to fine tune the pharmacokinetic or pharmacodynamic properties of a bioactive compound.

As used herein, molecules having "commonalities" or a "common structure", one to another, are considered to be essentially homologous to each other. This can be seen as one removes a bioisosteric group from a core structure. The core structures should remain the same, regardless of which bioisosteric group they are bound to. By way of non-limiting example, one tetrazole-pyrrolidone molecule and one pyrrolidone-carboxylate molecule would share a "common" pyrrolidone structure.

In the alternative, depending on context, the term "common" can be used herein to refer to multiple different molecules having essentially homologous properties, such as pharmaceutical properties, to each other. By way of non-limiting example, if a specific pharmaceutical property of two different bioisosteres is within +/−10% of one another, they would be considered as "common" to one another. In certain embodiments, if the specific pharmaceutical property of two different bioisosteres is within +/−5% of one another, they would be considered as "common" to one another.

As used herein, bioisosteres having calculated AED values that are "equivalent" to one another means that the respective values are close enough to one another such that a person of ordinary skill in the art would recognize such bioisosteres as likely to share common properties. By way of non-limiting example, if the AED values of two different bioisosteres are within +/−15% of one another, they would be considered as "equivalent" to one another. In certain embodiments, if the AED values of two different bioisosteres are within +/−10, 9, 8, 7, 6, 5, 4, 3, or 2% of one another, they would be considered as "equivalent" to one another.

The presently described subject matter relates to the confirmation and evaluation of various bioisosteres of a molecule, specifically 1,2,3-triazole and amides as bioisosteres to one another. More specifically, the present methods and systems relate to a new use of the Average Electron Density (AED) tool to assist in evaluating and confirming bioisosterism between a 1,2,3-triazole group and an amide group based on their respective AED values. Once the equivalent AED values between the 1,2,3-triazole group and the amide group are identified, it is possible to identify additional sets of atoms also having equivalent AED values to those of the first and second bioisosteres. Thus, the amide group or the 1,2,3-triazole group on the common core molecule structure can be replaced with one of the additional sets of atoms, and the new molecule would be expected to share common biological activity with the original molecule (s) evaluated.

In one embodiment, the present subject matter relates to a method for evaluating similarities between bioisosteres of a molecule, the method comprising: selecting a first molecule of interest having an amide group as a first bioisostere; replacing the amide group of the first molecule of interest with a 1,2,3-triazole group as a second bioisostere to obtain a second molecule having the second bioisostere; completing a quantum mechanics (QM) simulation for the first and second molecules containing first and second bioisosteres;

calculating average electron density (AED) values corresponding to the first and second bioisosteres in the first and second molecules; and confirming the experimentally observed bioisosterism between the 1,2,3-triazole group and the amide group based on the calculated AED values.

This approach permits the identification, evaluation, and classification of common bioisosteres using quantum methods. Previously, it was possible to evaluate and classify bioisosteres based on, for example, their respective Electrostatic Potential (ESP) maps. The present tool represents a new highly accurate and specific quantitative method for evaluating, measuring, classifying, and working with bioisosteres.

Bioisostere Selection

In a first step of the present methods and systems, a first molecule of interest having a first bioisostere is selected. In one non-limiting example, the first molecule of interest can include an amide group as a first bioisostere. This first bioisostere, in this example, the amide group, is then replaced on the first molecule of interest with a second suspected bioisostere, in this example, 1,2,3-triazole. This substitution will result in a second molecule having a second bioisostere, in this example, the 1,2,3-triazole. These first and second molecules, containing respective first and second bioisosteres, can then be further evaluated and analyzed.

Quantum Mechanics (QM) Simulation

Once two target bioisosteres for a particular molecule have been selected for further study, for example, a 1,2,3-triazole and an amide, a quantum mechanics (QM) simulation can be performed on the two molecules having two different bioisosteres of one another.

In one embodiment, the quantum mechanics (QM) simulation can be performed using Gaussian® software, for example, Gaussian 16, available from Gaussian, Inc. (Wallingford, CT), which is an electronic-structure modeling software that facilitates quantum chemistry calculations. Other QM software, such as Q-Chem (available from Q-Chem, Inc., Pleasanton, CA), The General Atomic and Molecular Electronic Structure System (GAMESS, maintained by members of the Gordon Research Group at Iowa State University, Ames, IA), or MolPro (available from the University of Stuttgart, Stuttgart, Germany) could be used. This QM analysis will obtain a wavefunction file from which the various properties of each molecule and bioisostere can be extracted. Therefore, the Gaussian 16 software is capable of completing a quantum mechanics (QM) simulation for each molecule and generating the wavefunction from which volumes and electron densities will be extracted after the QTAIM analysis.

Average Electron Density (AED)

The average electron density (AED) tool is based on the partitioning of a molecule into atomic basins using the quantum theory of atoms in molecules (QTAIM) partitioning scheme. The starting point of QTAIM is the topological analysis of the molecular electron-density distributions to extract atomic and bond properties that characterize every atom and bond in the molecule. These atomic and bond properties have considerable potential as bases for the construction of robust quantitative structure—activity/property relationships models. QTAIM is applicable to the electron density calculated from quantum-chemical calculations and/or that obtained from ultra-high resolution x-ray diffraction experiments followed by non-spherical refinement.

QTAIM allows the evaluation of properties of atoms in molecules, and subsequently bioisosteres in drug molecules. In QTAIM, the zero flux surfaces separate atoms into their own atomic basins. Then by operating different mathematical operators on the atomic basins, followed by numerical integrations, atomic properties of atoms in molecules can be evaluated. These properties include, volumes, charges, electron densities, areas, and average electron densities.

The average electron density (AED) is defined as the total electron population of a group of a molecule or of the full molecule divided by the corresponding volume. The internal interatomic limits between two atoms are determined by the internal zero-flux interatomic surfaces within the molecular interior, and the outer limit is set at the external 0.0004, 0.001, or 0.002 atomic unit isodensity envelope. The volumes and electron populations used to calculate the AED are those defined within Bader's quantum theory of atoms in molecules, a theory that partitions the molecular electron density into separate atomic basins separated by surfaces of zero-flux in the gradient vector field associated with the density. The atomic properties are then obtained by numerical integrations over each atomic basin. The AED properties of a specific molecular group are the sum of the properties of the atoms constituting this group.

The average electron density of a group is given by the formula:

$$\rho=\Sigma Ni/\Sigma Vi \quad (8)$$

where Ni is the electron population of each atom i, and Vi is the volume of each atom i.

In one embodiment, the wavefunction file obtained from the QM simulation can be further analyzed and processed using AIMAll software, from TK Gristmill Software (Overland Park, KS), based on the QTAIM theory. The AIMAll software package can be used for atomic integrations based on QTAIM. The interatomic basins can be delimited by zero-flux surfaces, and the outer limit of the atomic basins can be defined at three different isodensity envelopes of 0.0004, 0.001, or 0.002 a.u. AIMAll software is typically used for performing quantitative and visual QTAIM analyses of molecular systems, starting from molecular wavefunction data.

Likewise, AED values can be calculated by starting with, for example, a Gaussian software package, such as, for example, Gaussian16, with molecules optimized in the gas phase. In one embodiment, the level of theory used is the B3LYP density functional theory, namely B3LYP/6-311++ G(d,p)//B3LYP/6-311++ G(d,p) with ultrafine pruned (99, 590) grids and 'tight' self-consistent field optimization criteria. Vibrational frequency analysis was completed to confirm that the optimized geometries have no imaginary frequencies, in other words, they are not transition states. Here even if other (reasonable) details of the QM simulation are used, they will still give the same result.

In another embodiment, the Hershfield scheme may be used for partitioning the basins of atoms in molecules. The Hirshfeld (1977) method apportions the electron density among the atoms by the appropriate weighting. The weights are related by the atomic contribution to the promolecular density:

$$w_A(r)=\frac{\rho^A_{atm}(r)}{\rho_{pro}(r)}$$

The fragment of the density apportioned to atom A is $$p^A_{frag}(r)=w_A(r)p_{mol}(r)$$

An alternative scheme is based on the atomic contributions to the total promolecular potential $V_{pro}$ defined as the sum of the electronic and nuclear contributions.

In one embodiment of the present methods, AED values are determined for the bioisosteres of the molecules being studied. For example, in the study of the molecules having an amide group and a 1,2,3-triazole group, respectively, the AED values for the amide and 1,2,3-triazole groups were used for further analysis.

As can be seen, when the calculated AED values of the first bioisosteric group and the second bioisosteric group are equivalent to one another, it confirms that the two groups are indeed bioisosteres of one another. Here, since the AED values of the amide group, taken alone, and the 1,2,3-triazole group, taken alone, are equivalent to one another, the amide group and the 1,2,3-triazole group are confirmed as bioisosteres of one another. These methods will be effective regardless of whether the two bioisosteres being studied are attached to any additional $R_1/R_2$ groups or structures, or whether they are being studied as part of existing drug molecules. In this regard, the present methods are effective irrespective of the identity of any groups or structures to which the bioisosteres are attached, including but not limited to whether the bioisosteres are capped with a chlorine, benzene, or methyl group for either $R_1$ or $R_2$. Here, as shown below, the bioisosteres being studied must be attached to two R groups per bioisostere.

(a)

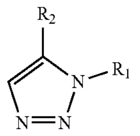

(b)

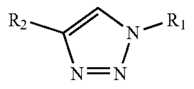

(c)

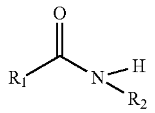

(d)

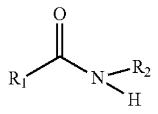

Shown above are 2D structures of (a) 1,5-triazole, (b) 1,4-triazole, (c) cis amide, and (d) trans amide. The ($R_1$, $R_2$) for each of (a)-(d) denote the capping groups, wherein, in this case each $R_1$ and $R_2$ can be a benzene, a methyl, or a chlorine group (based on their abundance use in drug molecules). As such, each of these bioisosteres can have three possible groups for $R_1$ and three possible groups for $R_2$, providing a combination of 9 different molecules tested for each of (a), (b), (c), and (d).

Likewise, the present methods are effective in evaluating bioisosterism even when the bioisostere of, for example, a drug molecule is docked in its receptor.

It has surprisingly been found that this analysis, evaluation, and procedure is effective for any two bioisosteres of one another, regardless of any different isomeric forms the respective bioisosteres might take. For example, when the bioisostere being studied is an amide group, the present methods are effective in classifying, evaluation, and confirming the bioisosterism for the amide group, regardless of whether the cis or the trans form of the amide group is being studied. Similarly, when the bioisostere being studied is a 1,2,3-triazole group, the present methods are effective in classifying, evaluation, and confirming the bioisosterism for the 1,2,3-triazole group, regardless of whether the 1,2,3-triazole has substitutions at the 1,4 or the 1,5 positions.

The ability of the AED tool to effectively be quantitively used in evaluating and confirming bioisosterism between two identified potential bioisosteres of one another stands in stark contrast to the Electrostatic Potential (ESP) map tool. While the ESP map tool has been used previously, it has several drawbacks associated therewith, including that the results of using this tool may be ambiguous and/or misleading, particularly as it is a qualitative rather than a quantitative tool. The results of the AED tool are sharper and clearer in demonstrating bioisosterism between two identified potential bioisosteres of one another.

New Bioisostere Discovery

In further embodiments, the present subject matter also relates to the use of the present methods in discovering new bioisosteres of a molecule.

By way of non-limiting example, one such embodiment relates to a method for discovering new bioisosteres of a molecule, the method comprising: selecting a first molecule of interest having an amide group as a first bioisostere; replacing the amide group of the first molecule of interest with a 1,2,3-triazole group as a second bioisostere to obtain a second molecule with the second bioisostere; evaluating similarities between the first bioisostere and the second bioisostere according to the methods using the quantum mechanics simulation and the calculated AED values, as herein described; identifying the calculated AED values equivalent between the first and second bioisosteres; identifying additional sets of atoms having calculated AED values corresponding to the calculated AED values equivalent between the first and second bioisosteres; and replacing the amide group of the first molecule of interest with one of the identified additional sets of atoms to obtain a third molecule with a third bioisostere.

As before, these methods will be effective regardless of which groups the bioisosteres being studied are attached to.

Drug Design

Once the present methods are performed to identify additional sets of atoms that may be useful as a new bioisostere, the new molecule having the new bioisostere can be further evaluated to determine any commonalities in biological properties or activity to the first bioisostere of the initial molecule of interest. For example, once the new molecule including the new bioisostere is confirmed to share common biological activity with the initial molecule including the first bioisostere, this new bioisostere is considered as likely to interact with the active site of the relevant receptor, thus speeding the drug design process by allowing the focus to be on those molecules most likely to be successful. Thus, the new molecule having the new bioisostere can be further investigated as a pharmaceutical of interest.

The screening process to determine potential drug candidates can be conducted according to any method known to those of ordinary skill in the art such as, for example, using high-throughput screening arrays. The present methods and systems can speed up what is commonly a long and difficult process by targeting specific bioisosteres of the selected molecules that are more likely to possess a desired activity, removing one or more steps from the typical screening process. The present methods and systems act as a filter to enrich the hit rate compared with typical random screening of bioisosteres of a given molecule, but not different molecules, although the latter is also possible.

EXAMPLES

Example 1—Procedure for Evaluating Bioisosterism Between an Amide Group and a 1,2,3-Triazole Group The following describes the methodology used for evaluating bioisosterism between an amide group and a 1,2,3-triazole group:

(a)

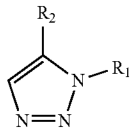

(b)

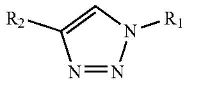

(c)

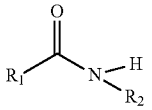

(d)

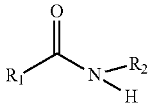

Three $R_1$ groups x three $R_2$ groups in each of the above bioisosteres (chlorine, benzene, and methyl) provided a combination of 9 different molecules tested for each of (a), (b), (c), and (d). QM optimizations were completed with Gaussian at the B3LYP density functional theory, namely B3LYP/6-311++ G(d,p)//B3LYP/6-311++ G(d,p) with ultrafine pruned (99,590) grids and 'tight' self-consistent field optimization criteria. Vibrational frequency analysis was completed to confirm that the optimized geometries have no imaginary frequencies, in other words, they are not transition states.

The AEDs of the bioisosteric groups (amide and triazole) were evaluated at three isodensity values (0.0004, 0.001, and 0.002 au) using the AIMAll package. The calculated AEDs at 0.001 au are summarized in FIG. 1, where what is reported includes the calculate values and standard deviations.

As can be seen by referring to FIG. 1, all three isodensities have similar trends. Both bioisosteres analyzed (triazole and amide) in either isomer were shown to have similar AED values. The calculated AED values clearly depict the similarities between bioisosteres, yet they differentiate subtle differences between isomers of each given bioisostere. In this regard, it is important to note that the volume values vary from amide to triazole, as do the electron populations, and even the charges, while the AED values remain similar to one another.

In addition, the small standard deviations for FIG. 1 show that the AED values are the same, irrespective of the change in the capping R groups.

The AIMAll package was used for atomic integrations based on QTAIM. The interatomic basins were delimited by zero-flux surfaces, and the outer limit of the atomic basins were defined at three different isodensity envelopes of 0.0004, 0.001 and 0.002 a.u.

The average electron density (AED) tool is based on the partitioning of the molecule into atomic basins using the quantum theory of atoms in molecules (QTAIM) partitioning scheme. The property of a bioisosteric group is the sum of the properties of the atoms constituting this group. The average electron density of a bioisosteric group is given by:

$$\rho=\Sigma Ni/\Sigma Vi \quad (8)$$

where Ni is the electron population of each atom i, and Vi is the volume of each atom i.

Example 2—Imatinib and its Analogue

Figure 2:
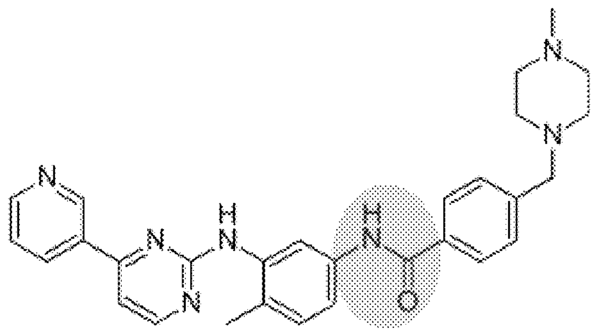
FIG. 2 shows a 2D structure of the imatinib drug molecule, where the amide that will be replaced with the triazole group is highlighted.

FIG. 2 shows a 2D structure of the imatinib drug molecule. The amide that was replaced with the triazole group as described herein is highlighted in FIG. 2. An analysis as described above was conducted, and the following results were obtained.

The amide in imatinib and its triazole-substituted analogue, respectively are reported in Table 1. The conformers of imatinib and its analogue were generated using Omega2 from the OpenEye Scientific software package, owned by Cadence Molecular Sciences (Santa Fe, NM). Omega conformational databases can be used as input to various applications, including shape comparison tools.

They were then docked, using OpenEye, into their receptor, the imatinib-ALB tyrosine kinase (PDB ID of complex is 2HYY). QM simulations using Gaussian16 (and using the same details as described above) were completed for the ligand (i.e., the drug or its analogue) from the top-ranked docked structure. The AED values of the bioisosteric groups (amide and triazole) were evaluated at three isodensity values (0.0004, 0.001, and 0.002 au) using the AIMAll package. The calculated AEDs at 0.001 au are summarized in Table 1, below.

TABLE 1

AED of the trans amide within imatinib, and 1,4-triazole within the imatinib analogue.

| Bioisosteric moiety | AED |
|---|---|
| trans amide in Imatinib | 0.0761 |
| 1,4-triazole in triazole analogue of Imatinib | 0.0742 |

As can be seen, the AED value for the trans amide in imatinib was very similar to that for the 1,4-triazole in the triazole analogue of imatinib.

It is to be understood that the methods and systems described herein are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for discovering new bioisosteres of a molecule, the method comprising:

selecting a first molecule of interest having an amide group as a first bioisostere;

replacing the amide group of the first molecule of interest with a 1,4-substituted or 1,5-substituted 1,2,3-triazole group as a second bioisostere to obtain a second molecule with the second bioisostere;

completing quantum mechanics (QM) simulations to obtain optimized geometries having no imaginary frequencies for the first and second molecules containing the first and second bioisosteres as docked in a receptor or as not docked in a receptor;

evaluating average electron density (AED) values, using an average electron density tool, corresponding to the first and second bioisosteres in the first and second molecules as docked in the receptor;

confirming experimentally observed bioisosterism between the 1,4-substituted or 1,5-substituted 1,2,3-triazole group and the amide group based on the calculated AED values;

identifying those calculated AED values equivalent between the first and second bioisostere, wherein the equivalent calculated AED values have a difference of no more than 10% between one another;

identifying additional sets of atoms having calculated AED values corresponding to the calculated AED values equivalent between the first and second bioisosteres, wherein the corresponding calculated AED values have a difference of no more than 10% from the equivalent calculated AED value of the first bioisostere;

computationally replacing the amide group of the first molecule of interest with one of the identified additional sets of atoms to obtain a third molecule with a third bioisostere; and screening the third molecule with the third bioisostere to determine whether the third molecule with the third bioisostere is a drug candidate having a desired biological activity.

2. The method of claim 1, wherein the screened third molecule with the third bioisostere is further evaluated to determine any commonalities in biological activity to the first molecule of interest having the first bioisostere.

3. The method of claim 1, wherein the screened third molecule with the third bioisostere shares common biological activity with the first molecule of interest having the first bioisostere.

4. The method of claim 1, wherein each bioisostere is considered in any isomeric form of the respective bioisostere.

5. The method of claim 1, wherein the calculated average electron density (AED) values are calculated as a sum of electron population divided by a sum of volumes of all atoms in the first or second bioisostere, wherein the electron population and the volumes of all atoms in the first or second bioisostere are obtained using quantum simulations.

6. The method of claim 1, wherein the screening of the third molecule with the third bioisostere comprises screening for new bioisosteres of the first molecule having one or more uses selected from the group consisting of:

1) identifying, generating, discovering, and creating new bioisosteres containing the additional sets of atoms having a desired biological activity for treating a specific disease;
2) identifying, generating, discovering, designing, and creating new molecules having a desired biological activity common to a biological activity of the first molecule;
3) filtering, identifying, and selecting molecules having a desired therapeutic effect to aid in drug design;
4) determining commonalities in biological activity between the first molecule and the third molecule, wherein when such commonalities in biological activity between the first molecule and the third molecule are found, further investigating the third molecule as a pharmaceutical of interest;
5) refining and improving one or more pharmacokinetic and pharmacodynamic properties of the first molecule selected from the group consisting of reducing sides effects, reducing toxicity, increasing half-life, improving an ADMET (absorption, distribution, metabolism, excretion, and toxicity) profile, improving solubility, improving stability, changing bond strength, varying rate of excretion to reduce damages, improving potency, increasing selectivity, and a combination thereof by replacing the first bioisostere of the first molecule with the additional set of atoms having a calculated AED values being within 90% or more of the AED of the first bioisostere;
6) providing an advancement in technology over existing software used in drug design and drug discovery;
7) reducing a number of molecules for further experimental testing;
8) saving time and money by providing a reduced number of hit candidates potentially having the desired biological activity; and
9) a combination thereof.

7. The method of claim 1, wherein an AED value of the simulated third molecule is identified according to a method comprising:

completing a QM simulation for the third molecule;

partitioning the third molecule into atoms;

delimiting the partitioned atoms by zero-flux surfaces to obtain interatomic basins;

delimiting an outer limit of the atomic basins with three different isodensity envelopes;

obtaining atomic basins and performing atomic integrations on the partitioned atoms of the third molecule;

extracting data for each of the partitioned atoms in the third molecule;

segregating a bioisosteric group of the third molecule from other atoms in the third molecule; and calculating AED values of the bioisosteric group of the third molecule.

8. The method of claim 1, wherein the additional sets of atoms having the corresponding calculated AED values having a difference of no more than 10% of the equivalent calculated AED value of the first bioisostere are identified according to a method comprising:

determining a first additional set of atoms;

replacing the set of atoms of the first molecule of interest with the first additional set of atoms to obtain one or more isomeric forms of a first potential candidate molecule;

completing a QM simulation for the first potential candidate molecule;

partitioning the first potential candidate molecule into atoms;

delimiting the partitioned atoms by zero-flux surfaces to obtain interatomic basins;

delimiting an outer limit of the atomic basins with three different isodensity envelopes;

obtaining atomic basins and performing atomic integrations on the partitioned atoms of the first potential candidate molecule;

extracting data for each of the partitioned atoms in the first potential candidate molecule;

segregating the first additional set of atoms of the first potential candidate molecule from other atoms in the first potential candidate molecule;

calculating AED values of the first additional set of atoms of the first potential candidate molecule;

confirming that the AED values of the first additional set of atoms of the first potential candidate molecule and the AED values corresponding to the first bioisostere in the first molecule are different from one another by no more than a predetermined 10%; and repeating these steps for one or more further additional set of atoms of each of one or more further potential candidate molecule until one or more potential candidate molecules, including the first potential candidate molecule, having identified additional sets of atoms having calculated AED values different by no more than a predetermined 10% of the calculated AED values of the first bioisostere is obtained.

9. The method of claim 8, wherein the calculated AED values of the first bioisostere and each of the additional sets of atoms are equivalent to one another, irrespective of any groups to which the first bioisostere and each of the additional sets of atoms are attached.

10. The method of claim 8, wherein the calculated AED values of the first bioisostere and each of the additional sets of atoms have capping groups.

11. The method of claim 8, wherein the step of completing a QM simulation for the first potential candidate molecule and each of the further potential candidate molecules optimizes the geometries, computes the frequency, and generates a wavefunction from which volumes and electron densities are extracted.

* * * * *